United States Patent [19]
Provonchee

[11] Patent Number: 5,989,403
[45] Date of Patent: Nov. 23, 1999

[54] ELECTROPHORESIS ASSEMBLY WITH FILLING MEANS

[75] Inventor: Richard B. Provonchee, Cushing, Mass.

[73] Assignee: FMC Corporation, Philadelphia, Pa.

[21] Appl. No.: 08/990,066

[22] Filed: Dec. 12, 1997

[51] Int. Cl.⁶ .................................................. G01N 27/26
[52] U.S. Cl. ........................................... 204/619; 204/618
[58] Field of Search .................................... 204/466, 467, 204/465, 615, 616, 618, 619, 620; 425/577, 403, 546; 249/141, 160; 264/267

[56] References Cited

U.S. PATENT DOCUMENTS 4,035,377  7/1977  Detroy ..................................... 204/619
4,417,967  11/1983  Ledley ..................................... 204/466

*Primary Examiner*—Jill Warden
*Assistant Examiner*—Alex Noguerda
*Attorney, Agent, or Firm*—J. R. Silverman; Ratner & Prestia

[57] ABSTRACT

The present invention provides a cassette with comb in place, useful for gel electrophoresis which is capable of being filled through a fluid conducting channel which communicates from the exterior of the top of the cassette assembly to the void (confined) volume of the cassette, for example, with the juncture between adjacent teeth of the comb; provides a comb useful for top filling of an electrophoresis cassette assembly and a method for top filling of an electrophoresis cassette assembly.

9 Claims, 5 Drawing Sheets

ELECTROPHORESIS ASSEMBLY WITH FILLING MEANS

BACKGROUND

This invention relates to an electrophoresis cassette and comb with filling means which enables the cassette with comb in place to be filled with the liquid electrophoretic medium. The cassette is useful for conducting gel electrophoresis. The invention also relates to a method for filling electrophoresis cassettes with the comb in place.

Electrophoresis is the resolution of a complex mixture of macromolecules on the basis of charge and/or size under the influence of an electric field. Usually, separation of the charged molecules is based on the strength of the electrical field and the net charge, size and shape of the molecules. The separation can also, at least in part, be affected by other parameters, such as isoelectric points, ionic strength, viscosity and temperature of the medium in which the charged molecules are moving. Since proteins and other biological molecules, such as DNA, RNA, enzymes, carbohydrates and the like are charged, electrophoresis techniques are ideal to separate them for analytical or preparative purposes.

It is common practice to use a cassette for conducting gel electrophoresis. The cassette comprises two flat plates, usually transparent glass or plastic, separated by spacing means and sealed along the sides and bottom edges to provide a void or confined space between the plates for placement of a suitable separation gel medium or electrophoresis gel such as agarose or a polyacrylamide in liquid form and its subsequent gelling or polymerization. When a separation is run on the gel in the cassette, the top portion of the gel is in contact with a buffered solution and the lower portion of the gel is in contact with a second buffered solution. An electric current is applied to the buffered solution(s) or the gel causing the migration and separation of the samples. By convention, the samples, for example, negatively charged proteins and nucleic acids, tend to run from the cathode (the top of the cassette, where the sample is placed) to the anode of the gel.

For the purposes of describing this invention, reference to the top of a cassette means the end of the cassette at which the wells are formed and in the instance of negatively charged samples, the cathode end of the gel. Additionally, the use of the terms "gelled" and "gel" refers to a solid state of the electrophoretic medium whether it be due to the cooling of an agarose gel or the polymerization of an acrylamide or acrylamide derivative.

In protein or nucleic acid fragment analysis, it is desirable to run more than one sample in a gel and to keep the samples separate. This is accomplished by sample separating means which is most commonly provided by the formation of wells at the sample-loading end of the gel. Sample wells are formed usually by means of a removable piece or "comb" with teeth having the desired shape of the wells and having straight (level) substantially perpendicular ends to the teeth. The comb is brought into contact with the liquid separation medium before it gels or polymerizes and is positioned so that the teeth extend into the liquid medium while it gels. After the gel has set, the comb is removed to leave wells where samples can be positioned. When conducting nucleic acid sequencing it is desirable to use a spacer, i.e., a comb with one tooth extending substantially across the width of the void or confined space, to create a straight edge to the resulting gel which edge is substantially perpendicular to the front and back plates of the cassette. Upon completion of the gelation of the electrophoretic medium, the comb (spacer) is removed and usually a saw-tooth configured (sharks-tooth) sample separator is inserted into the top of the cassette with the tip of the teeth touching or entering into the gel surface and the body of the teeth forming a reservoir for the samples to be analyzed. The samples enter the gel between the tips of the teeth. Often the sharks-tooth sample well configuration is the opposite side of the spacer. The term "comb" used to describe this invention, unless the context indicates otherwise, refers either to having one-tooth or -finger (a spacer) or a plurality of teeth or fingers.

To improve the separation of certain types of molecules, it is common practice to change the composition of the gel medium in the direction of the electrophoresis. This change in composition can, for example, take the form of a discontinuity formed by a stacking gel at the upper most portion of the gel and a resolving gel at the lower most portion of the gel. Another example of a change in composition is the commonly used gradient gel consisting of a continuous gradient or a discreet gradient of bands each of uniform but different composition or any combination of continuous and discreet gradient. In order to provide accurate sample resolution, it is necessary that the desired electrophoresis composition remain undisturbed until the gel medium has gelled or polymerized completely, particularly in the instance of stacking and/or gradient gels.

There are two commonly used methods for introducing the liquid separation medium into the cassette prior to polymerization, each with its own distinct advantages and disadvantages. Put simply, the solution can be introduced from the top of the cassette or from the bottom of the cassette.

When filled from the bottom of the cassette, the main advantage is that the comb can be in-place during the fill and the potential disruption during insertion of the comb of any desirable gradations or discontinuities to the liquid separation medium during filling is avoided. A disadvantage of the bottom fill is the need to gain access to the bottom of the cassette to introduce the gel medium. This access to the bottom of the cassette must be sealed until the liquid medium has gelled or leaking of the ungelled material will result. One attempt to minimize the disadvantage of the bottom fill method is exemplified by the commercially available gel casting apparatus by Hoefer Scientific called SE 275 Mighty Small Four-Gel Caster. Rather than effecting a seal with an opening in the bottom of a cassette, the Hoefer apparatus submerges an open bottomed cassette in a tub of liquid medium. Some of the liquid medium finds its way into the cassette. The cassette is left submerged in the tub of liquid medium until it has gelled at which time the cassette can be removed from the tub, cleaned up and used. This method, although producing a usable filled cassette, has the added disadvantage of wasting the polymerized gel medium that did not go into a cassette.

When filled from the top of the cassette, the main advantage is that the cassette can be filled without concern for sealing an opening until after the gel medium has polymerized. A disadvantage of the top fill is the requirement that the comb be placed into the cassette and into contact with the gel medium after the cassette is filled and thereby greatly increasing the risk of disturbing the gel during its formation, particularly any desirable gradations or discontinuities introduced into the gel medium during filling.

Although the above mentioned disadvantages for the bottom fill method and top fill method are real when making gels one at a time in the laboratory, they can be addressed to some extent by skill and careful attention to detail. It is when gels are made on a production scale that the disadvantages become pronounced. When using the bottom fill method, it is not easy to keep the bottom sealed during the gellation or polymerization step which can take as long as an hour. Any leakage not only ruins the cassette that is leaking, but also can create a mess on the production line. When a submerge-fill method is used, the attendant waste of gel medium and requirement to clean the cassettes are less than desirable.

Additionally, the uniformity of the gel is important to the quality of the separation obtained, for example, uniformity in the porosity of the gel or regions of the gel, uniformity (level and perpendicular to the plates) in the edge of the gel which first contacts the samples, uniformity in the thickness of the gel and uniformity (level and perpendicular to the plates) in the interface between discreet bands of gels (for example, between gradient gels or between stacking and resolving gels). Thus, it is desirable that the liquid gel-forming medium introduced into the cassette be disturbed as little as possible while gelling.

Accordingly, the present invention provides a cassette filling means for a cassette for gel electrophoresis that retains the advantages of the bottom fill method and the top fill method without the attendant disadvantages.

SUMMARY OF THE INVENTION

The present invention provides a means for filling an electrophoresis cassette with the comb in place from the top. For purpose of describing this invention, the electrophoresis cassette with comb in place is referred to as a cassette assembly. The filling means is a fluid conducting channel communicating between the top of the exterior of the cassette assembly and the top of the void or confined volume of the cassette. The fluid conducting channel is formed entirely in the comb or entirely in the cassette or partially in each.

The comb has a projection for contacting the liquid medium prior to its gellation to form a substantially horizontal level surface (described in relation to a vertical gel) to the gelled medium wherein the projection comprises one or a plurality of teeth extending from the central body of the comb and of sufficient length to extend into the confined or void space between the front and back plates of the cassette and preferably of sufficient width to extend substantially across the width of the confined space.

The present invention also provides combs useful in top filling of an electrophoresis cassette with comb in place and provides a process for top filling of an electrophoresis cassette with comb in place.

Other advantages to the present invention include the insertion of a comb into the cassette before the introduction of the liquid separation medium with no time or care considerations required for the forming gel.

DETAILED DESCRIPTION OF INVENTION

Figure 1:
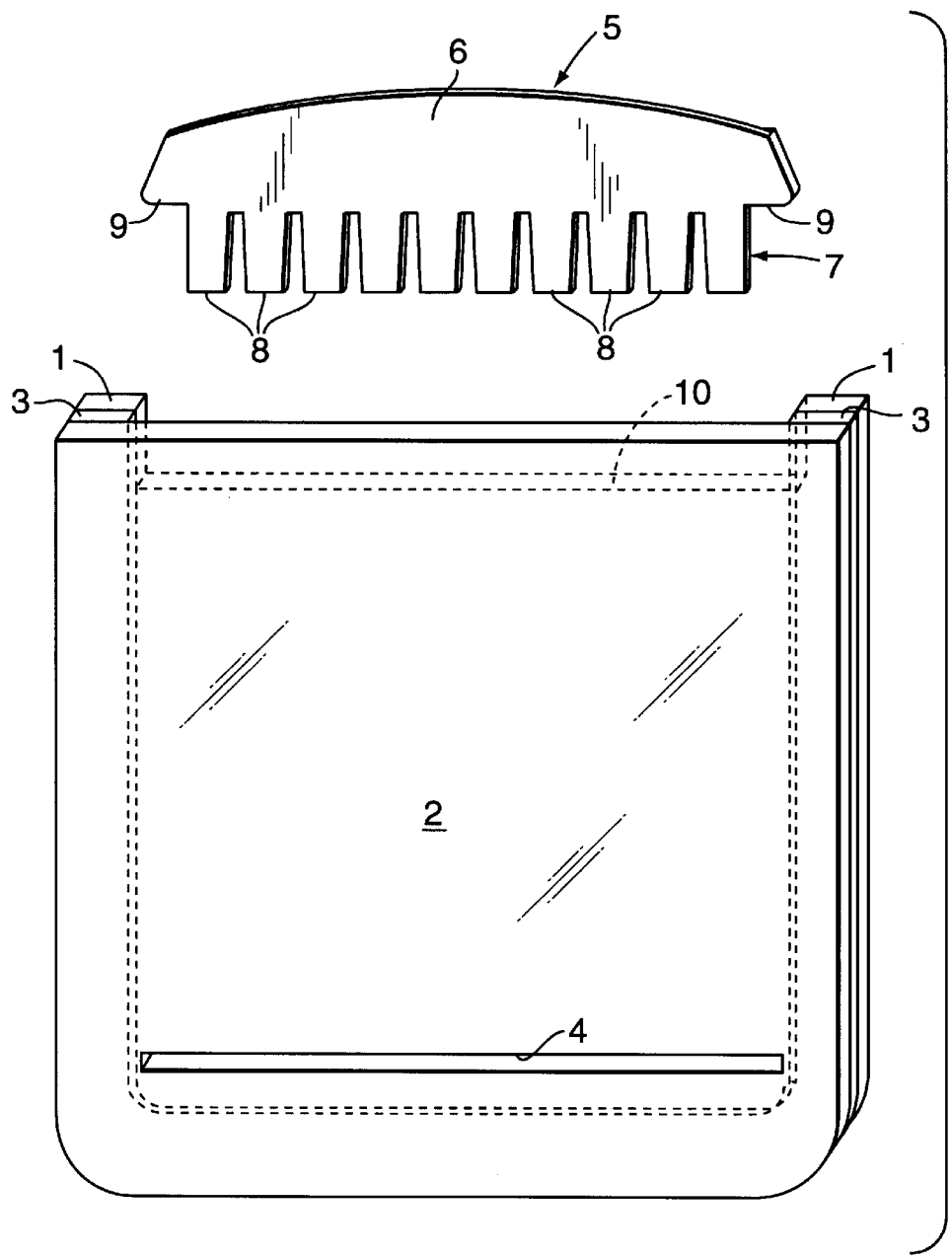
FIG. 1 is a pictorial view of the back of a commonly used electrophoresis cassette assembly.

FIG. 1 is representative of a commonly used electrophoresis cassette assembly which, with the comb removed, is generally used vertically in an electrophoresis chamber. It comprises a front plate 1 and back plate 2 having similar sizes, except the front plate is shorter than the back plate 2, with side and bottom edges. The shorter front plate 1 of the cassette enables the top of the gel to be in contact with a buffered solution and the cathode allowing an electric current to be conducted through the gel. The back plate 2 has a slot 4 (which is usually sealed during the filling of the cassette) which enables the bottom of the gel to be in contact with a buffered solution and the anode, thereby completing the conduction of an electrical current through the gel during electrophoresis. A spacer means 3 is positioned between the plates 1 and 2 and extends along the sides and bottom edges. The spacer means 3 is sealingly secured to the side and bottom edges to form a confined space (or void) 14 (marked on FIG. 3) between the plates into which the liquid separation medium, for example, an acrylamide or agarose, is placed or injected and allowed to polymerize or gel. Prior to polymerization or gelling of the liquid medium, there is inserted into the cassette and gelling medium a comb 5 having a central body 6 with a projection 7 comprising one or more teeth 8 (FIG. 1 shows a plurality of teeth) downward therefrom and capable of insertion into the gelling medium. The central body 6 extends laterally beyond the width of its projection 7 downward to about the juncture of the teeth (or tooth) optionally terminating to form shoulders 9 to engage the upper surface or top ridge 10 of the front plate 1. After the liquid separation medium has gelled completely, the comb is removed leaving a well where each tooth was. Many variations can be, and have been, made to this configuration of a cassette and still enable it to be used for electrophoresis.

Figure 2A:
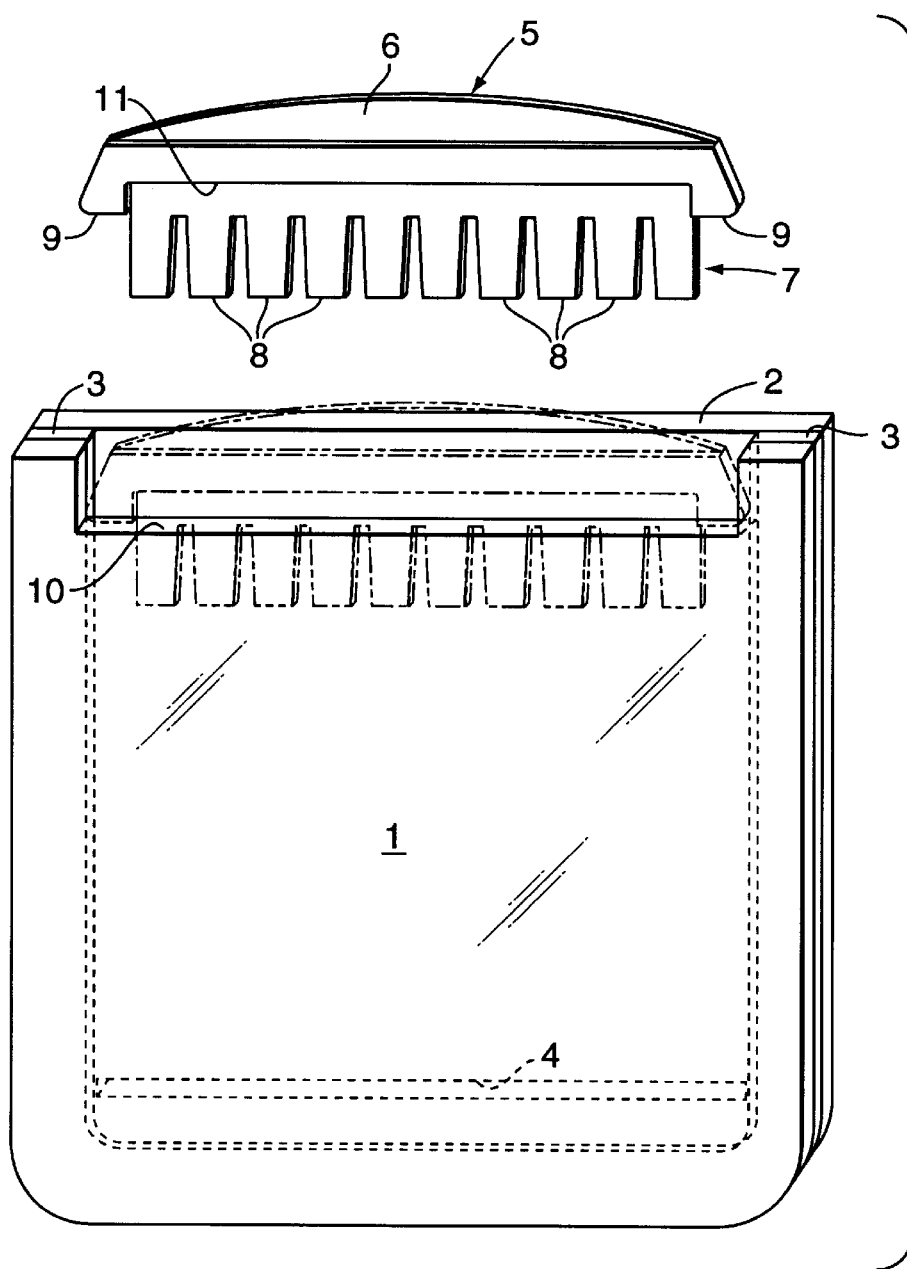
FIG. 2A is a pictorial view of the front of an electrophoresis cassette assembly of the present invention.
Figure 2B:
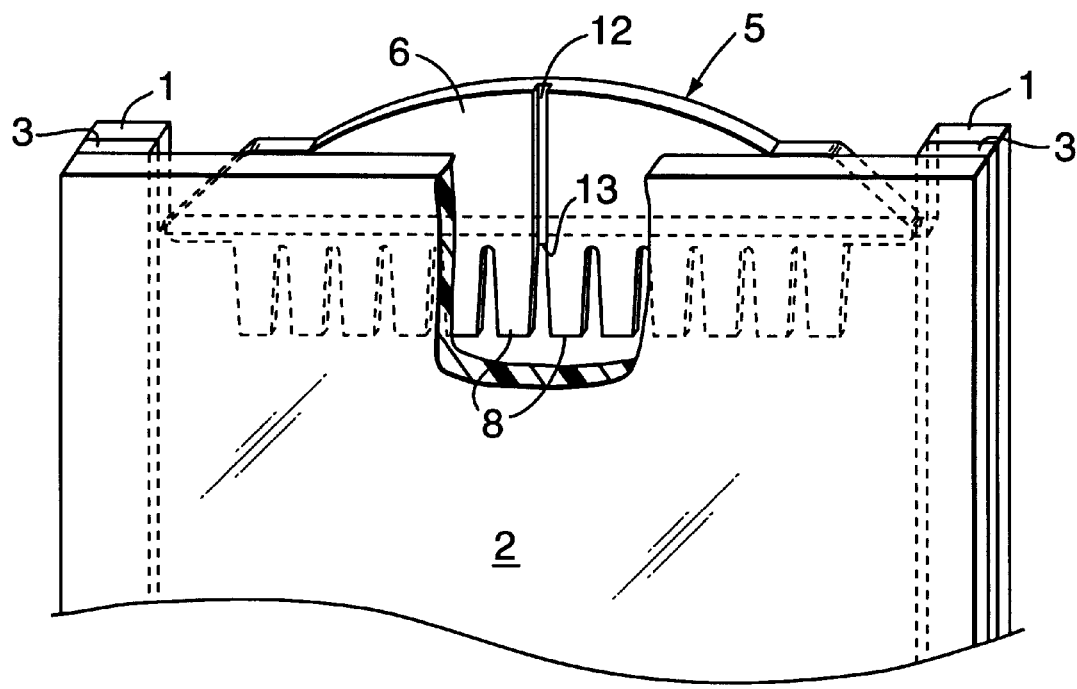
FIG. 2B is a pictorial view of a cassette assembly of the present invention using a cross-sectional view of the back plate of the cassette to show the fluid conducting channel in the comb.

The present invention will be described in terms of a vertical cassette and comb, recognizing that they can be varied by those in the art and still be useful in electrophoresis and the present invention. FIG. 2A is a front pictorial view of a comb, cassette and cassette assembly of the present invention with a spacer means 3 positioned between the plates 1 and 2 and extends along the sides and bottom edges. The spacer means 3 sealingly secured to the side and bottom edges to form a confined space (or void) between the plates into which the liquid separation medium, for example, an acrylamide or agarose, is placed or injected and allowed to polymerize or gel. Prior to placement in the cassette of the liquid separation means, there is inserted into the cassette a comb 5 having a central body 6 with a projection 7 comprising one or more teeth 8 (FIGS. 2A and 2B show a plurality of teeth) downward therefrom and capable of extension into the cassette's confined space. Preferably, the projection 7 has a narrower depth than the central body 6 thereby forming a ridge 11 which can engage the top surface or top ridge 10 of the front plate 1. In such an instance the central body 6 optionally extends laterally beyond the width of its projection 7 downward to about the juncture of the teeth (or tooth) terminating to form shoulders 9 which, when the projection 7 is narrower in depth than the central body 6 will engage the upper surface or top ridge 10 of the front plate 1. The ridge 11 then forms part of the shoulders 9 which go across the width of the comb. Or, preferably ridge 11 is elevated above all or a portion or portions of the juncture of the teeth (tooth) with the central body 6 facilitating the removal of the comb 5 from the gel and the cassette. The central body extends preferably substantially across the width of the confined space, and the tooth or teeth have a straight edge at their lower ends which, when inserted in the cassette, is substantially perpendicular to the front and back plates 1 and 2 of the cassette and substantially perpendicular to the sides of the confined space formed by the spacer means 3. The thickness of the tooth or teeth 7 is substantially equal to the distance between the back of the front plate 1 and the front of back plate 2 and preferably the thickness of the tooth or teeth (the projection) is less than the thickness of the central body 6. The comb is inserted until its shoulders 9 come into contact with the top ridge 10 of the front plate 1 causing the comb 5 to come to a stop. The shoulder 9 engages the upper surface of the front plate 1, when fully inserted, to properly position the comb 5 within the cassette. Thus, the shoulder 9 (or ridge 11) functions as a registry means enabling the comb to be inserted in one direction. Referring to FIG. 2B, there is shown a view of the back plate 2 of the cassette with the comb 5 inserted wherein the comb 5 has a fluid conducting channel 12 which is preferably located at about the middle of the central body 6 of the comb 5 and which channel communicates with the exterior of the top of the comb 5 or cassette assembly and at its lower end with the confined space of the cassette and preferably with the exterior of the juncture 13 between two adjacent teeth 8.

Figure 3:
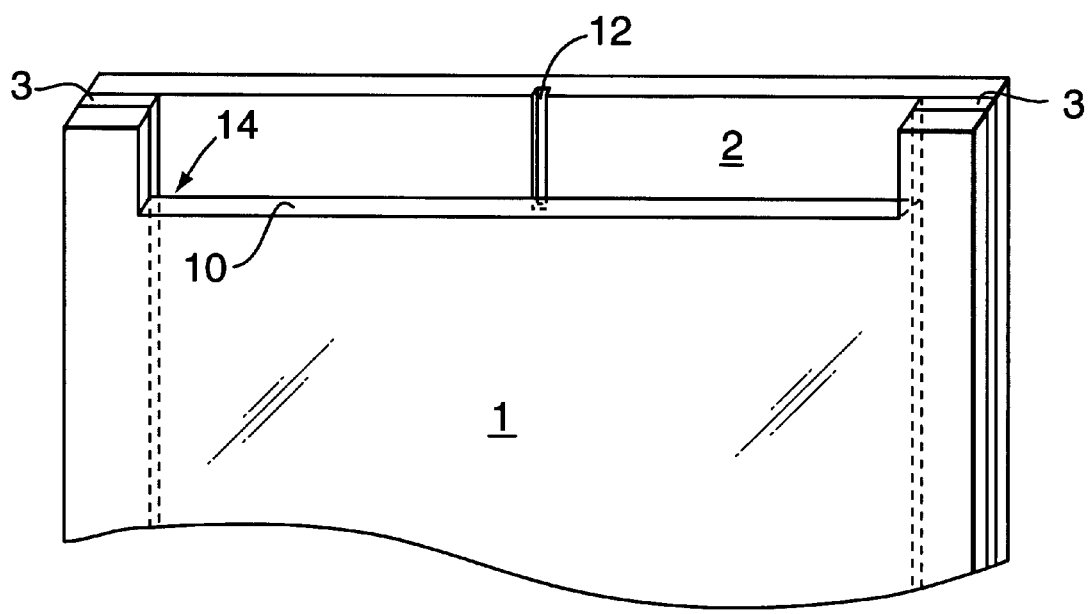
FIG. 3 is a pictorial view of the front of a cassette of the present invention showing the fluid conducting channel in the back plate of the cassette.

FIG. 3 shows the fluid conducting channel 12 in the back plate 2 of the cassette communicating from the exterior of the top of the back plate 2 of the cassette to the channel's 12 lower end which ends at a point at or below the level of gel desired in the cassette, for example, the top surface 10 of the front plate 1.

Figure 4A:
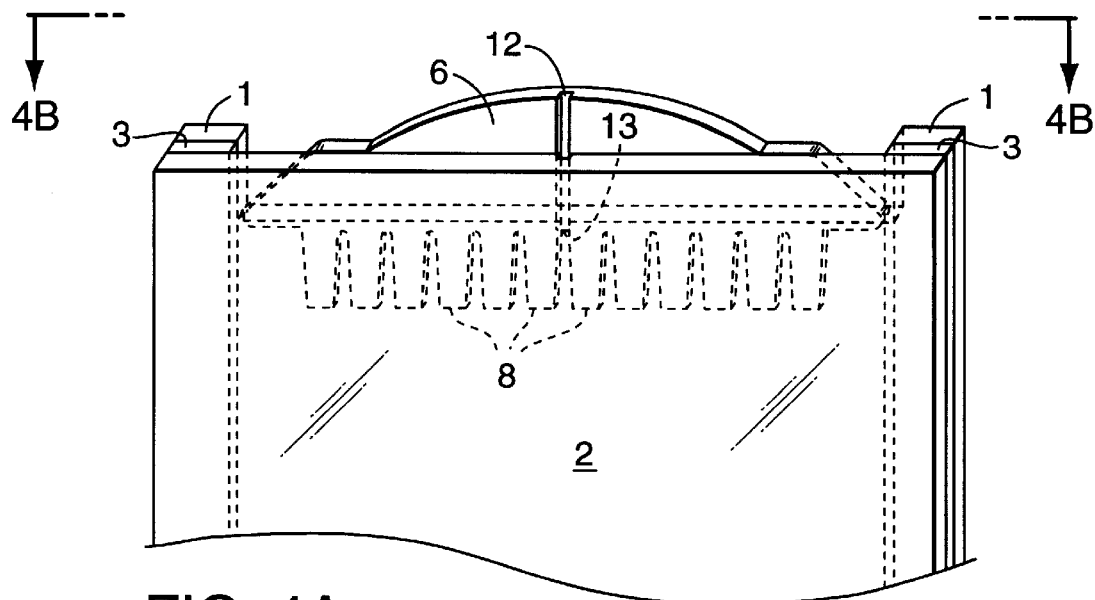
FIG. 4 is a pictorial of the cassette assembly of the present invention where the fluid conducting channel is formed in both the back central body of the comb and the back plate of the cassette.
FIG. 4B is a top view of FIG. 4A.
FIG. 4C is a cross-section taken on line 11—11 of FIG. 4B.
Figure 4B:
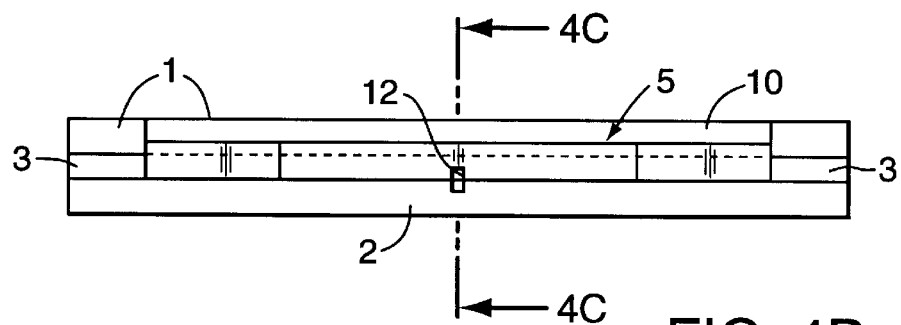

FIG. 4A shows the fluid conducting channel 12 formed in both the comb 5 and the back plate 2 of the cassette and communicating from the exterior of the top of the cassette assembly to the channel's 12 lower end at a point at or below (as shown in the figure) the juncture 13 of the tooth or teeth 8. FIG. 4B shows a cross-sectional view of the channel 12 in both the comb 5 and the back plate 2 which enables the depth of the fluid conducting channel to be greater than if it were only in the comb 5 or only in the back plate 2.

Figure 5A:
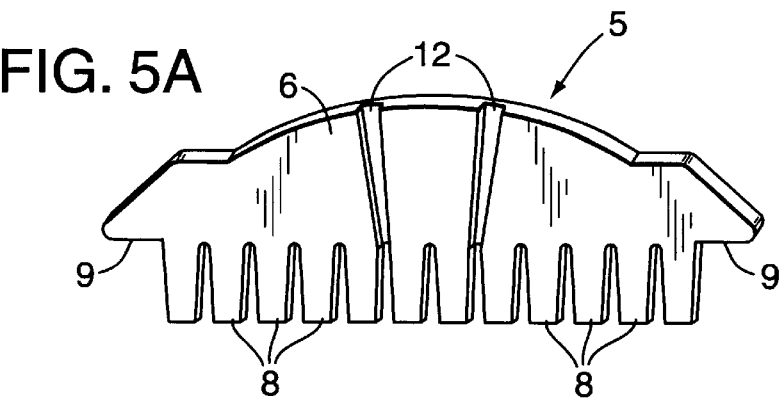
FIG. 5A is a pictorial view of the back of a multi-toothed comb having multiple fluid conducting channels.
Figure 5B:
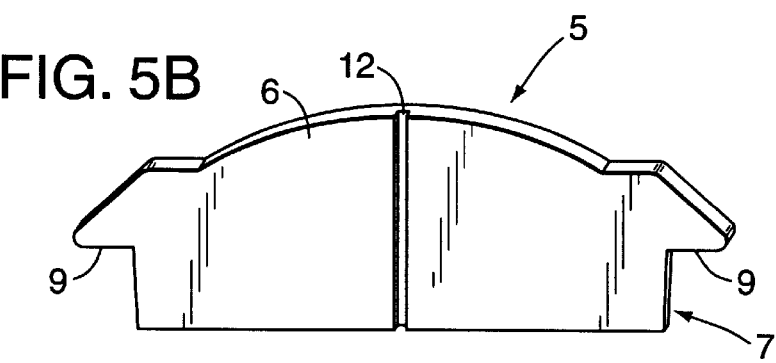
FIG. 5B is a pictorial view of the back of a one-tooth comb with a fluid conducting channel.
Figure 5C:
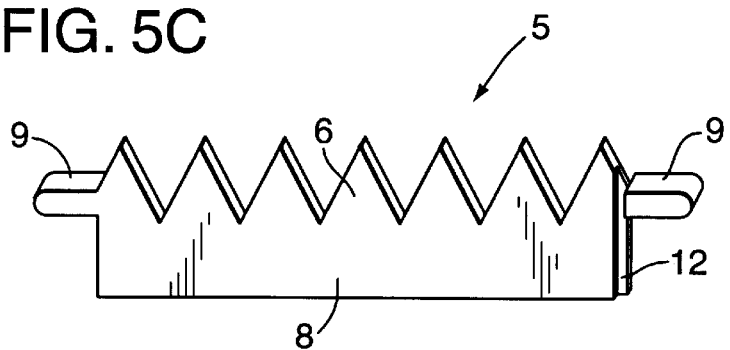
FIG. 5C is a pictorial view of a one-tooth comb with a fluid conducting channel which has a sharks-tooth configured central body.
Figure 5D:
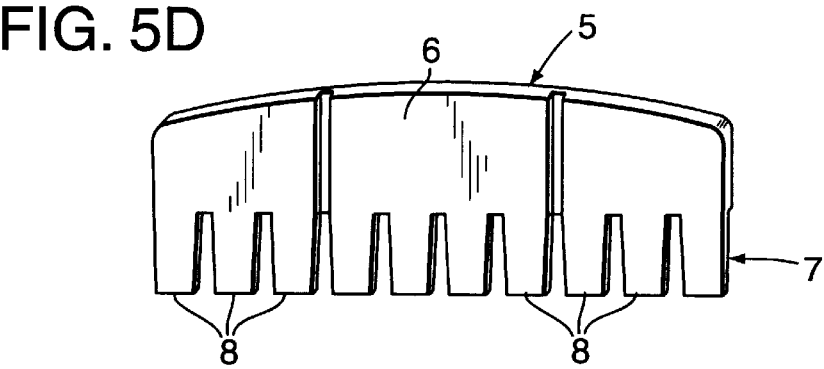
FIG. 5D is a pictorial view of a multi-toothed comb without shoulders with fluid conducting channels.

FIG. 5A shows a multi-toothed comb having two flared fluid conducting channels 12 in the back of a comb 5. FIG. 5B shows the back of a one-tooth comb 5 with one fluid conducting channel 12. FIG. 5C shows the back of a one-tooth comb 5 with one fluid conducting channel 11 which comb has a sharks-tooth configured central body 6. The central body 6 and the projection 7 (tooth 8) have the same depth thickness and shoulders 8 are somewhat thicker with the increased thickness occurring on the front side of comb 5. FIG. 5D shows the back of a multi-tooth comb 5 which has no shoulders and two fluid conducting channels 12. After the gel has set, this comb 5 can be pulled out of the gel and re-inserted upside down into the cassette with the sharks-teeth touching the gel or entering the gel forming sample wells. On all the figures, shoulders 9 as well as ridge 11 are optional and the variations in the combs, e.g. location of the fluid conducting channels, their configuration, the number of channels, configuration of the comb, can all be varied on each of the combs.

Figure 4C:
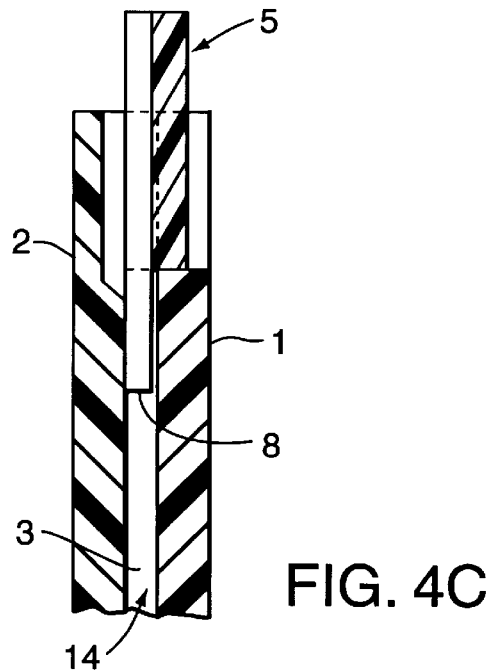

The form of the fluid conducting channel is not critical provided it allows for the injection or conduction of the liquid medium into the confined space of the cassette. The channel can be open or closed; it can be round, oval, square or oblong sided, or otherwise multi-sided (3 or more sides); and it can be the same side-to-side diameter its entire length or flared, preferably, at the top of the cassette assembly to facilitate the injection process. It can be a hole through the comb creating a channel or passage from the top of the comb, down through the comb and exiting at the bottom of the comb, e.g., a tooth or a juncture of the central body of the comb and a tooth. It can go down the back side of the comb (see, for example, FIG. 2B) or be located partially in the comb and partially in the back plate of the cassette (see, for example, FIG. 4). When at least a portion of the channel is located in the back plate 2 of the cassette, it may extend to just beneath the comb or the juncture of the central body of the comb and a tooth 13 all the way to the bottom of the confined space or some intermediary location. Having the channel the length of back plate 2 of the cassette may be desirable when injecting the liquid medium with a rigid injector, providing guidance in the insertion and placement of the injector and withdrawal as the liquid gelling medium is injected. A flexible injector may allow for its withdrawal as the liquid medium is injected without the need for the channel being the length or intermediate length of the cassette.

One or more channels, up to the number of teeth or junctures between teeth on a multi-toothed comb, can be used. Multi-channels may be particularly desirable when more than one liquid gelling or gelling medium is being injected, for example, in the placement of discontinuous or gradient separation mediums. When using from one to three channels, it is preferred they be located at about the center of the width of the top of the cassette. A centrally positioned channel allows for a more efficient filling of the cassette, and the filling of the cassette with the liquid medium is less apt to disturb the medium, particularly at the interface between stacking and resolving gels or to cause undesired mixing, for example, when inserting gradient mediums. When the fluid conducting channel is located in a comb having a plurality of teeth, it is preferred that the channel exits the bottom of the comb at the juncture of two teeth, preferably centrally located on the comb, to minimize any effect on the uniformity of the leading edge of the sample well(s).

The channel of this invention can be formed with the part during formation of the part or can be formed in the part as a secondary step.

The channel preferably exits the bottom of the comb as close to the center of the comb as practical thereby maximizing the advantage provided by a single centrally located fill point. The channel preferably exits the comb in the space between two adjacent teeth thereby minimizing the effect of the channel on any wells subsequently formed by the teeth. In the instance of a sharks-tooth comb, when it has a fluid conducting channel, it is preferably near the edge or side of the comb, see, for example, FIG. 5C.

The maximum depth of the channel as measured front to back is limited by the thickness and structural strength of the part in which it is formed. When the channel is formed solely in the comb or solely in the back plate of the cassette, the depth of the channel will be less than the thickness of the respective comb or back plate by an amount at least sufficient to maintain the useful integrity of the comb or back plate. When the channel is formed in both the comb and the back plate, the depth of the channel will be less than the combined thickness of the respective comb and back plate by an amount at least sufficient to maintain the useful integrity of the comb and back plate. This allows for a deeper depth to the channel (see, for example, FIG. 4C) enabling more efficient filling of the confined space. The minimum depth of the channel as measured from front to back is limited only by the requirement that the channel be useful for introducing gel medium into the cassette. Although the maximum depth of the channel will be dependent on the material in which it is formed, generally it will not be much greater than about one-half the thickness of the material.

The maximum practical width of the channel as measured from side to side is dictated by the distance between those teeth from between which the channel exits the comb. The minimum width of the channel as measured from side to side is limited only by the requirement that the channel be useful for introducing gel medium into the cassette.

When filling the cassette, the liquid medium is generally filled to the top of the teeth (or tooth) namely the juncture 13 of the tooth(s) 8 with the central body 6 of the comb 5. When the gel medium is a polyacrylamide, it is desirable to fill the cassette into a portion of the fluid conducting channel. This can help to decrease the liquid medium's exposure to air, specifically oxygen, while polymerizing to the polyacryamide. Oxygen inhibits that polymerization.

Any means which will conduct or inject the liquid separation medium into the cassette or cassette assembly can be used. Examples include a needle, a hollow blunt tipped injector, hose or tubing. The liquid separation medium is propelled by the use, for example, of a syringe, pump or by gravity means. The liquid separation media can be prepared using in-line mixing techniques and then injected into the cassette or first prepared and then propelled into the cassette injector means. Manual or automated systems can be used.

The cassette can be made of glass or a synthetic, usually plastic, material and the comb is made of a synthetic, usually plastic, material. The synthetic material must be compatible with the liquid and gelled separation medium system. Examples include acrylics such as polymethacrylate and polymethyl methacrylate, polystyrene, polycarbonate, polyethylene terephthalate, polyvinyl chloride, polyethylene, polymethyl polypropylene and cellulose acetates and their various copolymers.

The present invention also includes a method for top filling of an electrophoresis cassette having a comb in place comprising inserting an injection means into a fluid conducting opening which communicates between the exterior of the top of the cassette assembly and the confined space of the cassette assembly and propelling through the injection means and into the confined space of the cassette assembly a liquid separation medium capable of gelling and useful in electrophoresis. The fluid conducting opening can be a fluid conducting channel communicating at its lower end with a projection of the comb of the cassette assembly and at its upper end with the exterior of the cassette. The channel can be in the comb of the cassette assembly, in a plate, preferably back plate, of the cassette assembly or in both the comb and the plate. The fluid conducting opening can also be a space between the comb and edge of the cassette containing the spacer means of the cassette assembly which opening communicates at its upper end with the exterior of the cassette and at its lower end the confined space of the cassette.

The separation mediums used with the present invention are aqueous gel-forming polysaccahrides and acrylamide-based systems which are known to those in the electrophoresis art as are techniques for their preparation and use. Other gel and non-gel electrophoretic media known to those skilled in the art may be used without departing from the spirit of the invention. Useful aqueous gel-forming polysaccharides include, without limitation, agarose; glucomannan, especially glucomannan derived from konjac; partially deacetylated glucomannan; beta-1,3-glucans including curdlan; beta-carrageenan; furcellaran; agar (agar-agar); chemical derivatives of the foregoing; and mixtures thereof. Preferred gel-forming polysaccharides include agarose, allylglycidyl hydroxyethyl curdlan, and deacetylated konjac glucomannan are more preferred, and agarose is most preferred.

Acrylamide-based gels useful with the present invention include polymers formed from acrylamide and related acrylamide compounds such as N,N-dimethylacrylamide, N-methylacrylamide, N-methylolacrylamide, N,N'-methylenebisacrylamide (BIS), N,N'-propylenebisacrylamide (PBA), N,N'-oxydimethyleneacrylamide, 1,2-diacrylamide, ethylene diacrylate, 1,3-diacryloylethyleneurea, piperazine diacrylamide, N,N'-diallyltartardiamide, N-acryloylaminoethoxyethanol, N-acryloyl tris (hydroxymethyl)aminomethane, N-methylolacrylamide, and the like.

EXAMPLE

Two acrylamide mixtures comprising acrylamide, BIS (N,N,N',N'-methylenebisacrylamide)ammonium persulfate, TEMED (N,N,N',N'-tetramethylethylene diamine), a buffer, TBE (Tris-borate ethylenediaminetetraacetic acid) and water are prepared, one with 10 weight percent total acrylamides ("resolving gel") and one with 4 weight percent total acrylamides. (All ingredients are ultrapure or electrophoresis grade.) Each mixture is poured prior to polymerization into a cylinder of a 2-cylinder conventional gradient maker from which it is introduced into a cassette assembly through a fluid conducting channel at about the center of the comb. The fluid conducting channel exits the comb between two teeth at their juncture with the central body of the comb. After completion of the injection of the liquid polyacrylamide gels, the cassette assembly is left quienscently in its vertical position at room temperature until the liquid acrylamide mixture gels, at least 60 minutes. The comb is removed prior to using the gel for electrophoresis.

What is claimed is:

1. A cassette assembly for forming and using a polymerized gel in gel electrophoresis, comprising:

front and back plates having similar sizes with side and bottom edges;

spacer means positioned between the plates and extending along the side and bottom edges;

the spacer means sealingly secured to the sides and bottom edges of both plates to form a confined volume;

a comb having a central body from which a projection comprising a plurality of teeth extends downward therefrom capable of insertion into the confined volume; and a fluid conducting channel in the cassette assembly communicating at its lower end with the confined volume and at its upper end with the exterior of the cassette;

wherein the channel is formed entirely in the comb and the channel communicates at its upper end with the top of the comb and at its lower end with a juncture between adjacent teeth of the comb.

2. The cassette assembly of claim 1 wherein the tips of the teeth are level and are substantially perpendicular to the plates of the cassette when the comb is inserted into the cassette.

3. A cassette assembly for forming and using a polymerized gel in gel electrophoresis, comprising:

front and back plates having similar sizes with side and bottom edges;

spacer means positioned between the plates and extending along the side and bottom edges;

the spacer means sealingly secured to the sides and bottom edges of both plates to form a confined volume;

a comb having a central body from which a projection comprising a plurality of teeth extends downward therefrom capable of insertion into the confined volume; and a fluid conducting channel in the cassette assembly communicating at its lower end with the confined volume and at its upper end with the exterior of the cassette;

wherein the channel is formed entirely in one of the plates and the channel communicates at its upper end with the top of the comb and at its lower end with a juncture between adjacent teeth of the comb, and wherein the tips of the teeth are level and are substantially perpendicular to the plates of the cassette when the comb is inserted into the cassette.

4. A cassette assembly for forming and using a polymerized gel in gel electrophoresis, comprising:

front and back plates having similar sizes with side and bottom edges;

spacer means positioned between the plates and extending along the side and bottom edges;

the spacer means sealingly secured to the sides and bottom edges of both plates to form a confined volume;

a comb having a central body from which a projection comprising one tooth extends downward therefrom capable of insertion into the confined volume; and a fluid conducting channel in the cassette assembly communicating at its lower end with the confined volume and at its upper end with the exterior of the cassette;

wherein the channel is formed entirely in the comb and the channel communicates at its upper end with the top of the comb and at its lower end with a juncture between adjacent teeth of the comb, the comb has a registry means to assure the channel portions are in abutting relationship when the comb is inserted, and the channel is formed by abutting channel portions in the comb and one of the plates.

5. A comb for use in an electrophoresis cassette comprising a central body with a projection comprising at least one tooth and of sufficient length to enable its insertion into the cassette's confined space wherein the central body has a fluid conducting channel which communicates at its upper end with the exterior top of the comb and at its lower end a part of the projection, which when inserted into an electrophoresis cassette, is in the confined space of the cassette.

6. The comb of claim 5 wherein the projection has more than one tooth and fluid conducting channel communicates with the top of the comb and at its lower end with a juncture between adjacent teeth of the comb.

7. The comb of claim 5 wherein the thickness of the projection is less than the thickness of the central body.

8. The comb of claim 7 wherein the difference in thickness between the central body and projection occurs on the front side of the comb and wherein the fluid conducting channel is on the back side of the comb.

9. The comb of claim 8 wherein the difference in thickness between the central body and projection acts as a registry means enabling the comb to be positioned in only one direction in the cassette and to a maximum depth within the confined space of the comb.

* * * * *